United States Patent
Sato et al.

(10) Patent No.: US 11,491,467 B2
(45) Date of Patent: Nov. 8, 2022

(54) CATALYST FOR MANUFACTURING 1,3-BUTADIENE, MANUFACTURING METHOD OF CATALYST, AND MANUFACTURING METHOD OF 1,3-BUTADIENE

(71) Applicants: NATIONAL UNIVERSITY CORPORATION CHIBA UNIVERSITY, Chiba (JP); JGC Corporation, Yokohama (JP)

(72) Inventors: Satoshi Sato, Chiba (JP); Yuchao Wang, Chiba (JP); Kazunori Honda, Yokohama (JP)

(73) Assignee: NIPRO CORPORATION

( * ) Notice: Subject to any disclaimer, the term of this patent is extended or adjusted under 35 U.S.C. 154(b) by 3 days.

(21) Appl. No.: 16/970,015

(22) PCT Filed: Oct. 1, 2018

(86) PCT No.: PCT/JP2018/036713
§ 371 (c)(1),
(2) Date: Aug. 14, 2020

(87) PCT Pub. No.: WO2019/167323
PCT Pub. Date: Sep. 6, 2019

(65) Prior Publication Data
US 2021/0106978 A1    Apr. 15, 2021

(30) Foreign Application Priority Data
Mar. 2, 2018  (JP) .............................. JP2018-037868

(51) Int. Cl.
| | | |
|---|---|---|
| *B01J 23/10* | (2006.01) | |
| *B01J 21/04* | (2006.01) | |
| *B01J 21/08* | (2006.01) | |
| *B01J 21/18* | (2006.01) | |
| *B01J 27/224* | (2006.01) | |
| *B01J 37/08* | (2006.01) | |
| *C07C 1/24* | (2006.01) | |

(52) U.S. Cl.
CPC .............. *B01J 23/10* (2013.01); *B01J 21/04* (2013.01); *B01J 21/08* (2013.01); *B01J 21/18* (2013.01); *B01J 27/224* (2013.01); *B01J 37/088* (2013.01); *C07C 1/24* (2013.01); *C07C 2521/04* (2013.01); *C07C 2521/08* (2013.01); *C07C 2521/18* (2013.01); *C07C 2523/10* (2013.01); *C07C 2527/224* (2013.01)

(58) Field of Classification Search
CPC ..... C07C 1/24; C07C 11/167; C07C 2521/04; C07C 2521/08; C07C 2521/18; C07C 2523/10; C07C 2527/224; B01J 21/04; B01J 21/08; B01J 21/18; B01J 23/10; B01J 27/224; B01J 37/088
See application file for complete search history.

(56) References Cited

U.S. PATENT DOCUMENTS

| | | | |
|---|---|---|---|
| 10,322,978 B2 * | 6/2019 | Richard | .................. C07C 1/213 |
| 2005/0202963 A1 * | 9/2005 | Levin | ...................... B01J 23/10 |
| | | | 502/214 |
| 2016/0158729 A1 | 6/2016 | Racha et al. | |

FOREIGN PATENT DOCUMENTS

| | | |
|---|---|---|
| EP | 1961720 A1 | 8/2008 |
| JP | 2009023928 A | 2/2009 |
| JP | 2016516096 A | 6/2016 |
| JP | 2016204329 A | 12/2016 |
| JP | 2017508717 A | 3/2017 |
| JP | 2017186272 A | 10/2017 |
| WO | 2007083736 A1 | 7/2007 |
| WO | 2013183590 A1 | 12/2013 |

OTHER PUBLICATIONS

Igarashi, A. et al.: "Dehydration of 1,4-butanediol over lanthanide oxides", Catal. Commun., vol. 8, Sep. 20, 2006 (Sep. 20, 2006), pp. 807-810, XP005916733, doi:10.1016/j.catcom.2006.09.003.
Wang, Yuchao et al.: "Efficient generation of 1,3-butadiene by dehydration reaction of 3-buten-1-ol", Proceedings of the Forum A of the 120th Catalysis Society of Japan Meeting, Sep. 5, 2017 (Sep. 5, 2017), ISSN: 1343-9936.
Hirotomo Inoue et al.: "Dehydration of 1,4- butanediol over supported rare earth oxide catalysts", Applied Catalysis A: General 352 (2009) pp. 66-73.
S. Sato, R. Takahashi, T. Sodesawa and N. Yamamoto, "Dehydration of 1,4-butanediol into 3-buten-1-ol catalyzed by ceria", Catalysis Communications, 2004, vol. 5, p. 397-400.
D. Sun, S. Arai, H. Duan, Y. Yamada and S. Sato, "Vapor-phase dehydration of C4 unsaturated alcohols to 1,3-butadiene", Applied Catalysis A, 2017, vol. 531, p. 21-28.

* cited by examiner

*Primary Examiner* — Sharon Pregler
(74) *Attorney, Agent, or Firm* — Jordan and Koda, PLLC

(57) ABSTRACT

Provided is a technology for efficiently manufacturing 1,3-butadiene from 1,4-butanediol or 3-buten-1-ol in a reaction condition with a high conversion rate. A catalyst for manufacturing 1,3-butadiene, contains: ytterbium oxide as an active component for generating 1,3-butadiene from 1,4-butanediol or 3-buten-1-ol. In addition, a manufacturing method of 1,3-butadiene, includes: a step of obtaining a fluid containing 1,3-butadiene by bringing at least one of 1,4-butanediol and 3-buten-1-ol into contact with the catalyst for manufacturing 1,3-butadiene.

13 Claims, No Drawings

CATALYST FOR MANUFACTURING 1,3-BUTADIENE, MANUFACTURING METHOD OF CATALYST, AND MANUFACTURING METHOD OF 1,3-BUTADIENE

TECHNICAL FIELD

The present invention relates to a technology for manufacturing 1,3-butadiene.

BACKGROUND ART

A main manufacturing method of 1,3-butadiene that is used in a raw material of synthetic rubber, or the like is naphtha cracking in which 1,3-butadiene is manufactured as a co-product of ethylene by pyrolysis of naphtha. In addition, a single production process such as an oxidative dehydrogenation process of butene and a dimerization process of ethanol or acetaldehyde is also known.

A process for manufacturing 1,3-butadiene from 1,4-butanediol that can be manufactured from a biomass-derived raw material by a fermentation method or the like, or 3-buten-1-ol that is obtained by the dehydration of 1,4-butanediol has been variously developed as a single production process having a small environmental load.

However, the presence of a catalyst that is capable of advancing a reaction for generating 1,3-butadiene at a high selection rate, in a reaction condition with a high conversion rate, has not been found yet (Non-Patent Documents 1 and 2).

Here, in Patent Document 1, a manufacturing process including a first dehydration step of obtaining unsaturated alcohol from 1,3-butanediol, and a second dehydration step of obtaining 1,3-butadiene by dehydrating crotyl alcohol and 3-buten-2-ol that are distilled and separated from the unsaturated alcohol is described. Then, it is described that a catalyst to which ytterbium oxide ($Yb_2O_3$) is added to zirconia, as a dopant, may be used as a catalyst used in the first dehydration step.

However, in Patent Document 1, it is clearly stated that a by-product is generated due to the manufacturing of 1,3-butadiene using 1,4-butanediol as a raw material, and thus, a yield is not improved, and a technology for manufacturing 1,3-butadiene from 3-buten-1-ol is not described.

CITATION LIST

Patent Document

Patent Document 1: JP-A-2017-186272: claim 1, Paragraphs 0009, 0082 to 0090

Non-Patent Document

Non-Patent Document 1: S. Sato, R. Takahashi, T. Sodesawa and N. Yamamoto, "Dehydration of 1,4-butanediol into 3-buten-1-ol catalyzed by ceria", Catalysis Communications, 2004, volume 5, p. 397-400

Non-Patent Document 2: D. Sun, S. Arai, H. Duan, Y. Yamada and S. Sato, "Vapor-phase dehydration of C4 unsaturated alcohols to 1,3-butadiene", Applied Catalysis A, 2017, volume 531, p. 21-28

SUMMARY OF THE INVENTION

Technical Problem

The invention has been made in consideration of such circumstances, and an object thereof is to provide a technology for efficiently manufacturing 1,3-butadiene from 1,4-butanediol or 3-buten-1-ol in a reaction condition with a high conversion rate.

Solution to Problem

A catalyst for manufacturing 1,3-butadiene of the invention contains: at least ytterbium oxide as an active component for generating 1,3-butadiene from 1,4-butanediol or 3-buten-1-ol.

Here, the ytterbium oxide may be carried on a surface of a carrier containing at least one carrier raw material to be selected from a carrier raw material group including silica, α-alumina, carbon, and silicon carbide.

In addition, a manufacturing method of the catalyst for manufacturing 1,3-butadiene includes: a step of burning the ytterbium oxide or a precursor containing ytterbium at a temperature in a range of 600° C. or higher and 1000° C. or lower.

Further, a manufacturing method of 1,3-butadiene of the invention includes: a step of obtaining a fluid containing 1,3-butadiene by bringing a fluid containing 1,4-butanediol or a fluid containing 3-buten-1-ol into contact with the catalyst for manufacturing 1,3-butadiene.

Here, the fluid containing 1,4-butanediol or the fluid containing 3-buten-1-ol may be manufactured from a biomass-derived raw material by a fermentation method. In addition, it is preferable that the step of obtaining the fluid containing 1,3-butadiene is performed at a reaction temperature in a range of 300° C. or higher and 450° C. or lower. In addition, the manufacturing method of 1,3-butadiene may further includes: a step of burning the catalyst for manufacturing 1,3-butadiene at a temperature in a range of 600° C. or higher and 1000° C. or lower, before the step of obtaining the fluid containing 1,3-butadiene is implemented.

Advantageous Effects of the Invention

A catalyst for manufacturing 1,3-butadiene of the invention has high reaction activity for advancing a dehydration reaction from 1,4-butanediol or 3-buten-1-ol and a high selection rate for generating 1,3-butadiene, and thus, is capable of efficiently manufacturing 1,3-butadiene from such raw materials.

MODE FOR CARRYING OUT THE INVENTION

<Catalyst for Manufacturing 1,3-Butadiene>

A catalyst for manufacturing 1,3-butadiene (hereinafter, also referred to as "BD") of this embodiment contains ytterbium oxide as an active component, and the ytterbium oxide advances a dehydration reaction of Formula (1) described below in which BD is generated from 1,4-butanediol (hereinafter, also referred to as "1,4BDO").

[Chemical Formula 1]

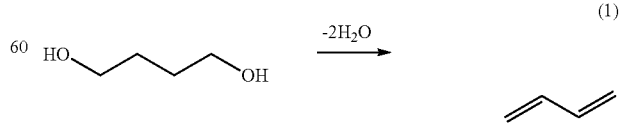

(1)

Ytterbium Oxide

Even though 1,4BDO advances the dehydration reaction, 1,4BDO is cyclized at a reaction temperature of a comparatively low temperature, and thus, tetrahydrofuran is easily generated, and in the case of increasing the reaction temperature, 1,4BDO decomposed into a C1 compound such as propylene or formaldehyde.

The catalyst for manufacturing BD of the invention is capable of attaining a single production process of BD from 1,4BDO, which was considered as difficult in the related art.

In addition, the ytterbium oxide has also activity for generating BD by further advancing a dehydration reaction with respect to 3-buten-1-ol (hereinafter, also referred to as "3B1OL") to be obtained by the dehydration reaction of 1,4BDO (Formula (2)).

[Chemical Formula 2]

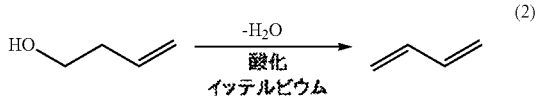

(2)

Ytterbium Oxide

The configuration or a preparation method of the ytterbium oxide contained in the catalyst for manufacturing BD is not particularly limited. Commercially available ytterbium oxide may be used, or ytterbium oxide obtained by burning a precursor containing ytterbium, such as ytterbium chloride, in an oxygen atmosphere may be used. In addition, for example, in a case where the precursor contains oxygen, the ytterbium oxide may be obtained even in the case of performing burning the precursor in a low oxygen atmosphere or an oxygen-free atmosphere. As an oxidized form of the ytterbium oxide, diytterbium trioxalate ($Yb_2O_3$) or an oxygen-deficient type thereof ($Yb_2O_{3-x}$ (for example, $0<X<1$)) is known, but other oxidized forms may be used. In addition, a composite oxide containing elements other than ytterbium, such as inevitable components in a manufacturing procedure, may be used as the oxidized form.

The ytterbium oxide, for example, may be contained in the catalyst for manufacturing BD in the form of fine particles in the order of nanometers to micrometers, from the viewpoint of being efficiently brought into contact with a raw material fluid of 1,4BDO or 3B1OL.

In the case of using fine particles-shaped ytterbium oxide, the fine particles-shaped ytterbium oxide may be carried on a carrier to configure the catalyst for manufacturing BD. In order to prevent a side product such as tetrahydrofuran or propylene described above from being generated, it is preferable to use a carrier not having reaction activity with respect to 1,4BDO or a carrier having a small specific surface area and not substantially affecting a reaction.

As such a carrier, a carrier containing at least one carrier raw material to be selected from silica, α-alumina, carbon, and silicon carbide can be exemplified.

The catalyst for manufacturing BD may have a configuration in which the ytterbium oxide is dispersed and carried on the surface of a powder-shaped carrier having a diameter larger than that of the fine particles of the ytterbium oxide. In addition, for example, the catalyst for manufacturing BD may have a configuration in which the ytterbium oxide is dispersed and carried on the surface of a carrier that is molded into the shape of particles or a ring.

A method for dispersing and carrying the ytterbium oxide on the carrier is not particularly limited. For example, a known carrying method such as an impregnation method, a precipitation method, and a kneading method can be used.

In the implementation of various carrying methods described above, the precursor of the ytterbium oxide may be carried on the carrier by using such methods, and then, the carrier may be burned, and thus, the precursor that is dispersed and carried on the surface of the carrier may be converted into the ytterbium oxide.

In addition, in a case where the catalyst for manufacturing BD after the ytterbium oxide is carried is in the shape of a powder, the catalyst for manufacturing BD may be molded into the shape of particles, a ring, or the like in accordance with a use mode in a manufacturing process of BD.

Here, it is preferable that the ytterbium oxide contained in the catalyst for manufacturing BD, for example, is burned at a temperature in a range of 600° C. or higher and 1000° C. or lower, preferably at a temperature in a range of 650° C. to 850° C. By performing the burning, it is possible to expose a specific crystal plane and to form a surface effective for this reaction.

Commercially available ytterbium oxide, ytterbium oxide having a low burning temperature at the time of forming the ytterbium oxide from a precursor, or the like is burned in the temperature range described above, and thus, it is possible to exhibit higher dehydration reaction activity. In addition, a burning temperature at the time of performing the burning for obtaining the ytterbium oxide from the precursor may be set to a temperature in a range of 600° C. or higher and 1000° C. or lower, and the formation of the ytterbium oxide and a treatment for exposing the crystal plane may be performed together.

A burning atmosphere, for example, may be an air atmosphere, or may be an inert gas atmosphere of nitrogen gas or the like.

In addition, the burning of the ytterbium oxide may be performed at any time before the reaction, and may be implemented at the time of manufacturing the catalyst or at a timing after a reactor for a manufacturing process of BD is filled with the ytterbium oxide.

<Manufacturing Method of 1,3-Butadiene>

A method for manufacturing BD from 1,4BDO or 3B1OL by using the catalyst for manufacturing BD described above will be described.

For example, a powder-shaped catalyst for manufacturing BD can be used in a reactor such as a fluidized-bed reactor, a suspended-bed reactor, or a movable bed reactor, and a catalyst for manufacturing BD that is molded into the shape of particles, a ring, or the like can be used in a fixed-bed reactor.

Here, in a case where a reactor containing the catalyst for manufacturing BD has sufficient heat resistance, a step of burning the catalyst for manufacturing BD at the temperature in the range of 600° C. or higher and 1000° C. or lower, preferably the temperature in the range of 650° C. to 850° C., described above, may be implemented as a pretreatment before the manufacturing of BD is started.

Then, a fluid of 1,4BDO or a fluid of 3B1OL, or a fluid containing both of 1,4BDO and 3B1OL is heated to a predetermined temperature and is supplied to the reactor containing the catalyst for manufacturing BD having a shape according to a reaction process. As a result thereof, a raw material fluid and the ytterbium oxide contained in the catalyst for manufacturing BD are brought into contact with each other in the reactor, and a dehydration reaction of 1,4BDO or 3B1OL is advanced, and thus, BD can be generated.

Here, 1,4BDO manufacturing by using sugar as a raw material, for example, a fermentation method using a smart cell can be used as 1,4BDO contained in the raw material fluid. In addition, 3B1OL obtained by dehydrating a part of such a biomass-derived 1,4BDO can also be used as a raw material of biomass-derived BD.

Note that, 1,4BDO contained in the raw material fluid is not limited to the biomass-derived 1,4BDO, and for example, may be manufactured in an industrial process for reacting acetylene with formaldehyde. Similarly, 3B1OL may be obtained by dehydrating apart of 1,4BDO manufactured in the industrial process.

The raw material fluid is heated in advance by using a heating furnace, a heat exchanger, or the like such that the temperature of the reactor, for example, is maintained to a temperate in a range of 300° C. or higher and 450° C. or lower, preferably a temperature in a range of 350° C. to 400° C.

In addition, a process variable such as a ratio of catalyst weight in the reactor to a supply flow rate of the raw material fluid (W/F, W: Catalyst Weight, F: Mass Flow Rate of Raw Material Fluid) and a superficial velocity (F'/S, F': Volume Flow Rate of Raw Material Fluid, S: Cross-Sectional Area of Reactor) is not particularly limited. For example, a preferred process variable may be suitably selected in accordance with the amount of production of BD in the manufacturing process of BD, a target conversion rate, or the like.

In addition, in order to improve a conversion rate of 1,4BDO or 3B1OL, a part of a fluid flowing out from the reactor may be extracted and converged into the raw material fluid, and may be supplied again to the reactor to be recycled.

The fluid flowing out from the reactor is shipped as a product BD after impurities are separated, for example, by being distilled.

According to the catalyst for manufacturing BD of this embodiment and the manufacturing method of BD using the catalyst for manufacturing BD, the following effects are obtained. The catalyst for manufacturing BD has high reaction activity for advancing the dehydration reaction from 1,4BDO or 3B1OL and a high selection rate for generating BD, and thus, is capable of efficiently manufacturing BD from such raw materials.

In particular, the catalyst for manufacturing BD of this example is capable of generating BD from 1,4BDO in one step, and has a high conversion rate of 1,4BDO or a high selection rate of BD, and thus, may be in raw material primary unit indicating a weight ratio of BD to be manufactured by a raw material per unit weight.

Then, the catalyst for manufacturing BD can be generated from 1,4BDO in one step, and thus, the configuration of the reactor can be simplified, and a simple BD manufacturing apparatus with less auxiliary equipment can be configured.

Further, BD is manufactured from the biomass-derived 1,4BDO or 3B1OL, and thus, a synthetic rubber raw material having a small environmental load can be provided as a green chemical product.

EXAMPLES (Test 1)

1,4BDO was brought into contact with ytterbium oxide, and a conversion rate of 1,4BDO and a selection rate of a generated substance were examined.

A. Test Condition

Commercially available ytterbium oxide (manufactured by KANTO CHEMICAL CO., INC., a purity of 99.95% or more) was burned in an air atmosphere of 800° C. for 3 hours, and a reactor was filled with 4 g of a ytterbium oxide powder after being burned, and then, a catalyst layer was heated to a predetermined temperature, and after that, 1,4BDO was supplied to the reactor. In components of a fluid flowing out from the reactor, a liquid component trapped by an ice water trap was analyzed by a gas chromatograph (Shimadzu (Registered Trademark, the same applies to the following) GC-2014) including a flame ionization detector (FID) every hour, and a gas component was analyzed by a gas chromatograph (Shimadzu GC-8A) including a thermal conductivity detector (TCD) online. A supply flow rate of 1,4BDO is 1.77 g/h, and a ratio (W/F) of the mass flow rate of 1,4BDO to the weight of ytterbium oxide is 2.26 h.

(Example 1-1) A reaction of 1,4BDO was performed at a reaction temperature of 300° C. In the test, the reactor was filled with unused ytterbium oxide, and the reaction was started, and then, the analysis was performed every hour, and thus, a conversion rate of 1,4BDO and a selection rate of each of the components were obtained from an average value after 2 hours and 5 hours of the reaction, on the basis of Expressions (3) and (4) described below.

Conversion Rate (%)=[{(Carbon-Based Molar Quantity of 1,4BDO Supplied to Reactor)−(Carbon-Based Molar Quantity of 1,4BDO Flowing out from Reactor)}/(Carbon-Based Molar Quantity of 1,4BDO Supplied to Reactor)]×100 (3)

Selection Rate (%)=[(Carbon-Based Molar Quantity of Aimed Component Flowing out from Reactor)/{(Carbon-Based Molar Quantity of 1,4BDO Supplied to Reactor)−(Carbon-Based Molar Quantity of 1,4BDO Flowing out from Reactor)}]100 (4)

(Example 1-2) The test was performed as with Example 1-1 except that a supply temperature of 1,4BDO was set to 320° C.

(Example 1-3) The text was performed as with Example 1-1 except that the supply temperature of 1,4BDO was set to 340° C.

(Example 1-4) The text was performed as with Example 1-1 except that the supply temperature of 1,4BDO was set to 360° C.

(Example 1-5) The text was performed as with Example 1-1 except that the supply temperature of 1,4BDO was set to 380° C.

B. Test Result

The results of Examples 1-1 to 1-5 are shown in Table 1. In addition to the abbreviations described above, "2B1OL" indicates 2-buten-1-ol, and "THF" indicates tetrahydrofuran. Here, each component of BD, 3B1OL, and 2B1OL includes each of a cis-isomer and a trans-isomer. In addition, components of "Others" include ethanol, 2-pentanone, 1-butanol, carbon dioxide, and other unspecific components.

TABLE 1

|  | Reaction temperature [° C.] | Conversion rate [%] | Selection rate [%] | | | | | |
| --- | --- | --- | --- | --- | --- | --- | --- | --- |
|  |  |  | BD | 3B1OL | 2B1OL | Propylene | THF | Others |
| Example 1-1 | 300 | 70.9 | 3.1 | 83.1 | 7.1 | 0.1 | 3.0 | 3.6 |
| Example 1-2 | 320 | 92.7 | 8.1 | 73.9 | 13.3 | 0.1 | 1.6 | 2.9 |
| Example 1-3 | 340 | 100.0 | 46.5 | 27.5 | 20.8 | 0.4 | 0.5 | 4.4 |
| Example 1-4 | 360 | 100.0 | 96.6 | 0.0 | 0.0 | 0.7 | 0.1 | 2.5 |
| Example 1-5 | 380 | 100.0 | 96.5 | 0.0 | 0.0 | 0.9 | 0.3 | 2.2 |

According to the test results shown in Table 1, the conversion rate of 1,4BDO also increased by increasing the reaction temperature, and 100% of 1,4BDO was changed to other substances at a temperature of 340° C. or higher.

In addition, the selection rate of BD also increased by increasing the supply temperature of 1,4BDO, and a high selection rate of 96% or more was obtained at a temperature of 360° C. or higher. On the other hand, the total selection rate of propylene, THF, and other components is suppressed to be less than 4%.

(Test 2)

The same test as Test 1 was performed by changing the ratio (W/F) of the weight of ytterbium oxide to the mass flow rate of 1,4BDO. The reaction temperature was 360° C.

(Example 2-1) The same test as Example 1-4 was performed except that W/F=0.14 was set.

(Example 2-2) The same test as Example 1-4 was performed except that W/F=0.28 was set.

(Example 2-3) The same test as Example 1-4 was performed except that W/F=0.56 was set.

(Example 2-4) The same test as Example 1-4 was performed except that W/F=1.13 was set.

B. Test Result

The results of Examples 2-1 to 2-4, and Example 1-4 are shown in Table 2. The description of the components in the table is the same as in Table 1.

TABLE 2

|  | W/F [h] | Conversion rate [%] | Selection rate [%] | | | | | |
| --- | --- | --- | --- | --- | --- | --- | --- | --- |
|  |  |  | BD | 3B1OL | 2B1OL | Propylene | THF | Others |
| Example 2-1 | 0.14 | 71.2 | 3.4 | 85.6 | 8.5 | 0.1 | 1.3 | 1.0 |
| Example 2-2 | 0.28 | 81.4 | 4.3 | 82.2 | 9.6 | 0.1 | 1.5 | 2.2 |
| Example 2-3 | 0.56 | 96.5 | 19.2 | 57.6 | 19.6 | 0.2 | 0.7 | 2.8 |
| Example 2-4 | 1.13 | 100.0 | 42.3 | 31.9 | 20.2 | 0.4 | 0.8 | 4.5 |
| Example 1-4 | 2.26 | 100.0 | 96.6 | 0.0 | 0.0 | 0.7 | 0.1 | 2.5 |

According to the test results shown in Table 2, the conversion rate of 1,4BDO also increased by increasing W/F (by increasing a filling amount of the ytterbium oxide in the reactor), and 100% of 1,4BDO was changed to other substances at W/F of 1.13 h or more. In addition, the selection rate of BD also increased by increasing W/F, and a high selection rate of 96% or more was obtained at W/F of 2.26.

(Test 3)

3B1OL was brought into contact with various rare-earth metal oxides, and a conversion rate of 3B1OL and the selection rate of the generated substance were examined. A test condition was the same as that of Test 1 except that a supply flow rate of 3B1OL was 1.47 g/h, and a ratio (W/F) of a mass flow rate of 3B1OL to the weight of the rare-earth metal oxide was 2.72 h. The reaction temperature was 340° C.

(Example 3-1) Ytterbium oxide was used as the catalyst.

(Comparative Example 3-1) Erbium oxide was used as the catalyst.

(Comparative Example 3-2) Dysprosium oxide was used as the catalyst.

(Comparative Example 3-3) Samarium oxide was used as the catalyst.

(Comparative Example 3-4) Cesium oxide was used as the catalyst.

B. Test Result

The results of Example 3-1 and Comparative Example 3-1 to Comparative Example 3-3 are shown in Table 3. The description of the components in the table is the same as in Table 1. Here, ether is straight-chain unsaturated ether represented by $C_8H_{14}O$, and components of "Others" include butanol, methanol, 3-buten-2-ol, carbon dioxide, and other unspecific components.

TABLE 3

| | Catalyst (Active component) | Conversion rate [%] | Selection rate [%] | | | | |
|---|---|---|---|---|---|---|---|
| | | | BD | 2B1OL | Propylene | Ether | Others |
| Example 3-1 | $Yb_2O_3$ | 99.6 | 96.7 | 0.7 | 0.8 | 0.1 | 1.7 |
| Comparative Example 3-1 | $Er_2O_3$ | 81.2 | 73.1 | 19.9 | 1.3 | 1.3 | 1.7 |
| Comparative Example 3-2 | $Dy_2O_3$ | 76.7 | 69.7 | 22.3 | 1.7 | 1.5 | 4.8 |
| Comparative Example 3-3 | $Sm_2O_3$ | 60.4 | 59.7 | 31.2 | 1.7 | 2.3 | 5.1 |
| Comparative Example 3-4 | $CeO_2$ | 81.0 | 43.9 | 8.9 | 2.1 | 6.9 | 38.2 |

According to the test results shown in Table 3, the ytterbium oxide had a high conversion rate of 3B1OL compared to other rare-earth oxides, and a high selection rate of BD of 96% or more was obtained.

As considered in Tests 1 and 2 described above, it is found that the conversion rate of 1,4BDO and the selection rate for generating BD from 1,4BDO are affected by both of the reaction temperature and W/F. Accordingly, even at the reaction temperature of Examples 1-1 to 1-3 wherein the conversion rate of 1,4BDO or the selection rate of BD is small compared to Examples 1-4 and 1-5, it can be said that it is possible to further increase the conversion rate or the selection rate of BD by further increasing the value of W/F (by increasing the filling amount of the ytterbium oxide, by decreasing the flow rate of 1,4BDO).

It can also be said that it is possible to further increase the conversion rate or the selection rate of BD even at W/F corresponding to Examples 2-1 to 2-4 by further increasing the reaction temperature.

In addition, as found from a comparison between Example 3-1 and Comparative Example 3-1 to Comparative Example 3-3, the ytterbium oxide is effective for the dehydration reaction of not only 1,4BDO but also 3B1OL to BD, and it is possible to attain a high conversion rate and a high selection rate of BD by selecting a preferred reaction condition.

In addition, in this test, the reactor is filled with commercially available ytterbium oxide. Thus, the ytterbium oxide is dispersed and carried on a carrier, and a contact efficiency between 1,4BDO and/or 3B1OL and the ytterbium oxide is improved, and therefore, it is possible to improve the conversion rate of 1,4BDO and/or 3B1OL or the selection rate of BD.

As a guide for efficiently producing BD, the reaction temperature, W/F, the dispersed and carried state of the ytterbium oxide with respect to the carrier, or the like may be adjusted such that the conversion rate of 1,4BDO and/or 3B1OL is 50% or more, preferably 80% or more, and the selection rate of BD is 80% or more, preferably 90% or more.

(Test 4)

The catalyst (the active component) to be brought into contact with 1,4BDO was changed, and the conversion rate of 1,4BDO and the selection rate of the generated substance were examined. Note that, the following test is based on the description of Non-Patent Document ("S. Sato et al., Catalysis Communications, 5(2004)397.") published by the present inventors.

A. Test Condition (Comparative Example 4-1) The reactor was filled with 0.2 g of commercially available alumina (DC-2282, manufactured by Diamond Catalyst Co., Ltd.) powder, and then, the alumina powder was burned in a helium atmosphere of 500° C. for 1 hour, and was used in the reaction test. The catalyst layer was heated to 200° C., and then, 1,4BDO was supplied at 1.79 g/h, and the components of the fluid flowing out from the reactor were analyzed. The conversion rate of 1,4BDO and the selection rate of each of the components were obtained from an average value after 5 hours from the start of the reaction, on the basis of Expressions (3) and (4) described below.

(Comparative Example 4-2) The same test as that of Comparative Example 4-1 was performed except that the supply temperature of 1,4BDO was set to 425° C.

(Comparative Example 4-3) The same test as that of Comparative Example 4-1 was performed except that commercially available silica alumina (N631-L, manufactured by JGC Catalysts and Chemicals Ltd.) was used.

(Comparative Example 4-4) The same test as that of Comparative Example 4-3 was performed except that the supply temperature of 1,4BDO was set to 425° C., and a filling amount of the silica alumina powder was set to 0.3 g.

(Comparative Example 4-5) The same test as that of Comparative Example 4-1 was performed except that zirconia prepared by hydrolysis of zirconyl nitrate was used, a filling amount of a zirconia powder was set to 0.3 g, and the supply temperature of 1,4BDO was set to 425° C.

(Comparative Example 4-6) The same test as that of Comparative Example 4-1 was performed except that magnesium oxide prepared by a citrate process using magnesium nitrate and a citric acid as a raw material was used, and the supply temperature of 1,4BDO was set to 425° C.

(Comparative Example 4-7) The same test as that of Comparative Example 4-1 was performed except that commercially available ceria (manufactured by Wako Pure Chemical Industries, Ltd.) was used, and a filling amount of a ceria powder was set to 0.3 g.

(Comparative Example 4-8) The same test as that of Comparative Example 4-7 was performed except that the supply temperature of 1,4BDO was set to 450° C.

B. Test Result

The results of Comparative Examples 4-1 to 4-8 are shown in Table 4. The description of the components in the table is the same as in Table 1. Note that, components of "Others" in Table 4 include 2B1OL, 2-butenal, 1-butanol, 2-hydroxytetrahydrofuran, and γ-butyrolactone.

TABLE 4

|  | Catalyst (Active component) | Reaction temperature [° C.] | Conversion rate [%] | Selection rate [%] | | | |
|---|---|---|---|---|---|---|---|
|  |  |  |  | BD | 3B1OL | THF | Others |
| Comparative Example 4-1 | $Al_2O_3$ | 200 | 17.3 | 69.5 | 0.0 | 30.5 | 0.0 |
| Comparative Example 4-2 |  | 425 | 100.0 | 3.1 | 0.0 | 91.8 | 5.1 |
| Comparative Example 4-3 | $SiO_2$—$Al_2O_3$ | 200 | 26.6 | 67.2 | 0.0 | 32.8 | 0.0 |
| Comparative Example 4-4 |  | 425 | 99.8 | 2.7 | 0.1 | 92.6 | 4.6 |
| Comparative Example 4-5 | $ZrO_2$ | 425 | 100.0 | 3.0 | 9.8 | 78.3 | 8.9 |
| Comparative Example 4-6 | MgO | 425 | 7.5 | 5.4 | 5.6 | 27.3 | 61.7 |
| Comparative Example 4-7 | $CeO_2$ | 275 | 6.3 | 87.4 | 0.0 | 0.0 | 12.6 |
| Comparative Example 4-8 |  | 450 | 94.9 | 24.8 | 25.9 | 7.6 | 41.7 |

According to the results shown in Table 4, in the case of using alumina, silica alumina, zirconia, and ceria, as the catalyst, except for magnesium oxide, the conversion rate of 1,4BDO was 90% or more at a reaction temperature of 425° C. or higher. However, the component obtained as a result thereof was 3B1OL or THF, and other components, and thus, the selection rate of BD was less than 25% (Comparative Examples 4-2, 4-4, 4-5, and 4-8).

Compared to the results of Comparative Examples, the ytterbium oxide used in Tests 1 and 2 can be evaluated as a catalyst that is capable of advancing the dehydration reaction for efficiently generating BD from 1,4BDO and/or 3B1OL in a reaction condition with a high conversion rate.

The invention claimed is:

1. A manufacturing method of 1,3-butadiene, the method comprising:
   a step of obtaining a fluid containing 1,3-butadiene in one step by bringing a fluid containing 1,4-butanediol into contact with a catalyst for manufacturing 1,3-butadiene,
   wherein the catalyst contains ytterbium oxide as an active component, and
   wherein a ratio of active component weight of the catalyst to a supply flow rate of the 1,4-butanediol (W/F) is to achieve at least 96% conversion of 1,4-butanediol and at least 19% selectivity for 1,3-butadiene.

2. The manufacturing method of 1,3-butadiene according to claim 1,
   wherein the fluid containing 1,4-butanediol is manufactured from a biomass-derived raw material by a fermentation method.

3. The manufacturing method of 1,3-butadiene according to claim 1,
   wherein the step of obtaining the fluid containing 1,3-butadiene is performed at a reaction temperature in a range of 300° C. or higher and 450° C. or lower.

4. The manufacturing method of 1,3-butadiene according to claim 1, further comprising:
   a step of burning the catalyst for manufacturing 1,3-butadiene at a temperature in a range of 600° C. or higher and 1000° C. or lower, before the step of obtaining the fluid containing 1,3-butadiene is implemented.

5. The manufacturing method of 1,3-butadiene according to claim 1, wherein the ytterbium oxide is carried on a surface of a carrier containing at least one carrier raw material to be selected from a carrier raw material group including silica, α-alumina, carbon, and silicon carbide.

6. The manufacturing method of 1,3-butadiene according to claim 1, wherein the ratio of W/F is 0.56 h or more.

7. A manufacturing method of 1,3-butadiene, the method comprising:
   a step of obtaining a fluid containing 1,3-butadiene by bringing a fluid containing 3-buten-1-ol into contact with a catalyst for manufacturing 1,3-butadiene,
   wherein the catalyst contains ytterbium oxide as an active component, and
   wherein a ratio of active component weight of the catalyst to a supply flow rate of the 3-buten-1-ol (W/F) to achieve at least 90% selectivity of 1,3-butadiene.

8. The manufacturing method of 1,3-butadiene according to claim 7,
   wherein the fluid containing 3-buten-1-ol is manufactured from a biomass-derived raw material by a fermentation method.

9. The manufacturing method of 1,3-butadiene according to claim 7,
   wherein the step of obtaining the fluid containing 1,3-butadiene is performed at a reaction temperature in a range of 300° C. or higher and 450° C. or lower.

10. The manufacturing method of 1,3-butadiene according to claim 7, further comprising:
    a step of burning the catalyst for manufacturing 1,3-butadiene at a temperature in a range of 600° C. or higher and 1000° C. or lower, before the step of obtaining the fluid containing 1,3-butadiene is implemented.

11. The manufacturing method of 1,3-butadiene according to claim 7, wherein the ytterbium oxide is carried on a surface of a carrier containing at least one carrier raw material to be selected from a carrier raw material group including silica, α-alumina, carbon, and silicon carbide.

12. The manufacturing method of 1,3-butadiene according to claim 7, wherein the ratio of W/F to which the selectivity to 1,3-butadiene reaches 96% or more.

13. A manufacturing method of 1,3-butadiene, the method comprising:
    a step of obtaining a fluid containing 1,3-butadiene by bringing a fluid containing 3-buten-1-ol into contact with a catalyst for manufacturing 1,3-butadiene,
    wherein the catalyst contains ytterbium oxide as an active component, and wherein a ratio of active component weight of the catalyst to a supply flow rate of the 3-buten-1-ol (W/F) is 0.56 or more.

\* \* \* \* \*